United States Patent
Nalesnik

(10) Patent No.: US 8,664,442 B2
(45) Date of Patent: Mar. 4, 2014

(54) ANTI-OXIDANTS

(75) Inventor: Theodore E. Nalesnik, Hopewell Junction, NY (US)

(73) Assignee: Chemtura Corporation, Middlebury, CT (US)

( * ) Notice: Subject to any disclaimer, the term of this patent is extended or adjusted under 35 U.S.C. 154(b) by 952 days.

(21) Appl. No.: 12/283,170

(22) Filed: Sep. 9, 2008

(65) Prior Publication Data

US 2010/0062955 A1 Mar. 11, 2010

(51) Int. Cl.
| | | |
|---|---|---|
| *C07C 211/00* | (2006.01) | |
| *C10M 141/06* | (2006.01) | |
| *C10M 171/00* | (2006.01) | |
| *C01G 39/06* | (2006.01) | |
| *C07C 211/58* | (2006.01) | |
| *C07F 7/22* | (2006.01) | |
| *C10M 135/36* | (2006.01) | |
| *C10M 137/10* | (2006.01) | |
| *C10M 105/34* | (2006.01) | |
| *C10M 173/02* | (2006.01) | |
| *C10M 141/10* | (2006.01) | |

(52) U.S. Cl.
USPC ........... 564/305; 508/151; 508/167; 508/556; 508/382; 508/251; 508/371; 508/463; 508/513; 508/379; 508/421

(58) Field of Classification Search
None
See application file for complete search history.

(56) References Cited

U.S. PATENT DOCUMENTS

| | | | | |
|---|---|---|---|---|
| 3,026,322 A | * | 3/1962 | Shcok | 546/163 |
| 3,278,436 A | * | 10/1966 | Dazzl | 508/145 |
| 4,824,601 A | | 4/1989 | Franklin | |
| 5,498,809 A | | 3/1996 | Emert et al. | |
| 2005/0230664 A1 | | 10/2005 | Duyck et al. | |
| 2006/0223722 A1 | * | 10/2006 | Rowland | 508/444 |
| 2007/0265178 A1 | | 11/2007 | Patil et al. | |

FOREIGN PATENT DOCUMENTS

| | | |
|---|---|---|
| DE | 3230718 A1 | 3/1983 |
| EP | 0072575 A | 2/1983 |
| SU | 7558012 | 8/1980 |

OTHER PUBLICATIONS

Gomez Aranda et al. Revista de la Academia de Ceincias Exactas, Fisicas, Quimica y Naturales de Zargoza, 1973, 28(2), 215-224 (Derwent abstract).*
The International Search Report and The Written Opinion of the International Searching Authority mailed Aug. 13, 2009.

* cited by examiner

*Primary Examiner* — Clinton Brooks
(74) *Attorney, Agent, or Firm* — Joseph Suhadolnik; George Romanik

(57) ABSTRACT

A dialkylanilino-cyclohexane compound useful as an anti-oxidant has the following formula I or formula II:

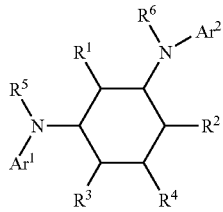

wherein $Ar^1$ and $Ar^2$ can be the same or different and each is an alkylaromatic group; each of $R^1$, $R^2$, $R^3$, and $R^4$ is independently selected from hydrogen or $CR^7R^8$; each of $R^5$, $R^6$, and $R^7$ is independently selected from hydrogen and a substituted or unsubstituted $C_1$ to $C_{32}$ hydrocarbyl group; and each $R^8$ is independently selected from hydrogen and a $C_1$ to $C_2$ alkyl group, provided that when, each of $R^1$ and $R^2$ is $CR^7R^8$ and each such $R^8$ is other than hydrogen, $R^1$ and $R^2$ may be joined to form a five or six-membered ring, and provided further that when, each of $R^3$ and $R^4$ is an adjacent $CR^7R^8$ and each such $R^8$ is other than hydrogen, $R^3$ and $R^4$ may be joined to form a five or six-membered ring.

23 Claims, 1 Drawing Sheet

ANTI-OXIDANTS

FIELD

This invention relates to anti-oxidants, their method of preparation, and their use particularly, but not exclusively, as additive for lubricant compositions.

BACKGROUND

Lubricating oils as used in, for example, the internal combustion engines of automobiles or trucks are subjected to a demanding environment during use. This environment results in the oxidation of the oil catalyzed by the presence of impurities in the oil, such as iron compounds, and is also promoted by the elevated temperatures experienced by the oil during use. This catalyzed oxidation of the oil not only contributes to the formation of corrosive oxidation products and sludge in the oil but can also cause the viscosity of the oil to increase or even cause the oil to solidify. This oxidation of lubricating oils during use is usually controlled to some extent by the use of antioxidant additives which may extend the useful life of the oil, for example, by reducing or preventing unacceptable viscosity increases.

Among the additives that are known to be effective in extending the life of lubricating oils are phenolic antioxidants and aminic antioxidants. Phenolic antioxidants contain one or more sterically hindered phenol functionalities, and can be either used alone or in synergistic combination with other additives, such as alkylated aminic antioxidants. Aminic antioxidants contain one or more nitrogen atoms and typically comprise alkylated diphenyl amines and phenothiazines. The synthesis and uses of phenolic antioxidants, phenothiazines and alkylated diphenyl amines have been reported in the literature.

For example, it is known from U.S. Pat. No. 4,824,601 to produce a liquid antioxidant composition by reaction of diphenylamine with diisobutylene in a molar ratio from 1:1.1 to 1:2.5 in the presence of an acid-activated earth catalyst, at a reaction temperature of at least 160° C. The reaction product is a mixture of t-butylated diphenylamines; t-octylated diphenylamines; and (iii) higher alkylated diphenylamines, in which the content of 4,4'-di-t-octyldiphenyl-amine in the final reaction mass, excluding catalyst, is below 25% by weight and that of diphenylamine is below 10% by weight. The product is said to be an excellent anti-oxidant for lubricants and functional fluids of mineral oil and synthetic origin.

In addition, U.S. Patent Publication No. 2005/0230664 discloses a lubricant anti-oxidant mixture prepared by the partial condensation of an alkylated diphenylamine with an aldehyde or ketone in the presence of an acidic catalyst to yield at least one acridan of the general formula:

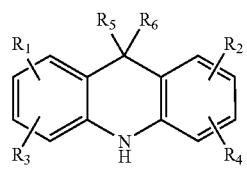

wherein: $R_1$, $R_2$, $R_3$, and $R_4$ are independently selected from the group consisting of hydrogen, $C_3$ to $C_{32}$ alkyl, and $C_3$ to $C_{32}$ alkenyl, provided that at least one of $R_1$, $R_2$, $R_3$, and $R_4$ is not hydrogen, and $R_5$ and $R_6$ are independently selected from the group consisting of $C_1$ to $C_{20}$ hydrocarbyl and hydrogen; wherein, at the termination of said condensation, residual alkylated diphenylamine is not separated from the acridan product.

In addition, of the many commercially available amine anti-oxidants Naugalube® 403 is supplied by Chemtura Corporation and is N,N'-di-sec-butyl-p-phenylene diamine of the following formula:

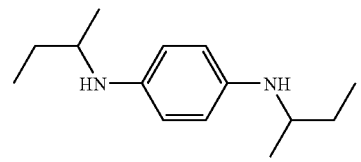 [SMILES: CCC(C)Nc1ccc(NC(C)CC)cc1]

There is, however, a continuing need for new antioxidants and antioxidant systems which offer improved performance and which are effective at low levels. There are a number of factors which have contributed to this continuing need. One such factor is that in recent years internal combustion engines are often operated at even higher temperatures, which tend to increase the rate of oxidation and shorten the useful life of the oil. In addition, there is a strong desire to use cheaper base stocks for lubricating oil compositions which have inferior resistance to oxidation and require more efficient and effective antioxidants. There is also a need for lubricating oils to have a longer in service life span to support the longer service intervals for motor vehicles.

According to the present invention, a novel class of dialkylanilino-cyclohexane compounds has now been prepared, which compounds have been found to exhibit advantageous anti-oxidant properties when used alone or with other additives in lubricant formulations, fuel formulations and rubber compositions.

1,4-Bis(phenylamino)cyclohexane is a known compound and, according to Russian Patent No. 755,812, is useful in combination with hydroquinone in increasing the scorch resistance of synthetic rubbers.

SUMMARY

In one aspect, the present invention resides in a dialkylanilino-cyclohexane compound having the following formula I or formula II:

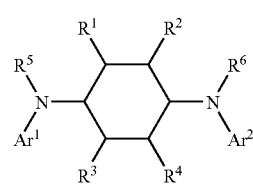

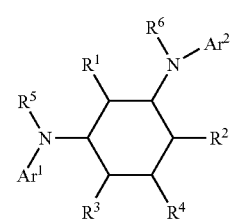

wherein $Ar^1$ and $Ar^2$ can be the same or different and each is an alkylaromatic group; each of $R^1$, $R^2$, $R^3$, and $R^4$ is independently selected from hydrogen or CR⁷R⁸; each of R⁵, R⁶, and R⁷ is independently selected from hydrogen and a substituted or unsubstituted $C_1$ to $C_{32}$ hydrocarbyl group; and each R⁸ is independently selected from hydrogen and a $C_1$ to $C_2$ alkyl group, provided that when, each of R¹ and R² is CR⁷R⁸ and each such R⁸ is other than hydrogen, R¹ and R² may be joined to form a five or six-membered ring, and provided further that when, each of R³ and R⁴ is an adjacent CR⁷R⁸ and each such R⁸ is other than hydrogen, R³ and R⁴ may be joined to form a five or six-membered ring.

Conveniently, each of R¹, R², R³, and R⁴ is hydrogen.

Conveniently, each of Ar¹ and Ar² is an alkylaromatic group in which the alkyl group is a $C_1$ to $C_{30}$ alkyl group, such as a $C_2$ to $C_{20}$ alkyl group.

Conveniently, each of Ar¹ and Ar² is an alkylaromatic group in which the alkyl group is in the para-position relative to the nitrogen atom attached to the alkylaromatic group.

Generally, each of Ar¹ and Ar² is the same alkylaromatic group.

In one embodiment, the dialkylanilino-cyclohexane compound is selected from para-di(para-n-butylanilino)-cyclohexane, para-di(para-n-hexylanilino)-cyclohexane and para-di(para-n-dodecylanilino)-cyclohexane.

In a further aspect, the invention resides in a process of producing the dialkylanilino-cyclohexane compound of said one aspect, the process comprising the step of reacting under reductive alkylation conditions at least one compound of the formula III:

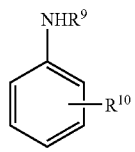

III wherein R⁹ is R⁵ or R⁶ and R¹⁰ is a $C_1$ to $C_{30}$ alkyl group with a compound of the formula IV or V:

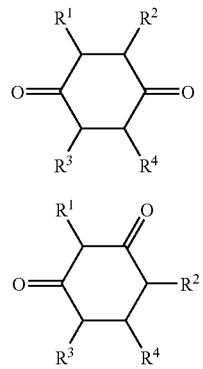

IV

V

In yet a further aspect, the invention resides in a lubricating oil composition comprising (a) a base lubricant and (b) a dialkylanilino-cyclohexane compound having the formula I or II, typically in an amount between about 0.1 wt % and about 10 wt % of the total lubricating oil composition.

In still yet a further aspect, the invention resides in a fuel composition comprising (a) a base fuel and (b) a dialkylanilino-cyclohexane compound having the formula I or II, typically in an amount between about 10 ppm and about 1000 ppm of the total fuel composition.

In another aspect, the invention resides in a rubber composition comprising (a) a base rubber and (b) a dialkylanilino-cyclohexane compound having the formula I or II, typically in an amount between about 0.5 wt % and about 8.0 wt % of the total rubber composition.

DETAILED DESCRIPTION OF THE EMBODIMENTS

Figure 1:
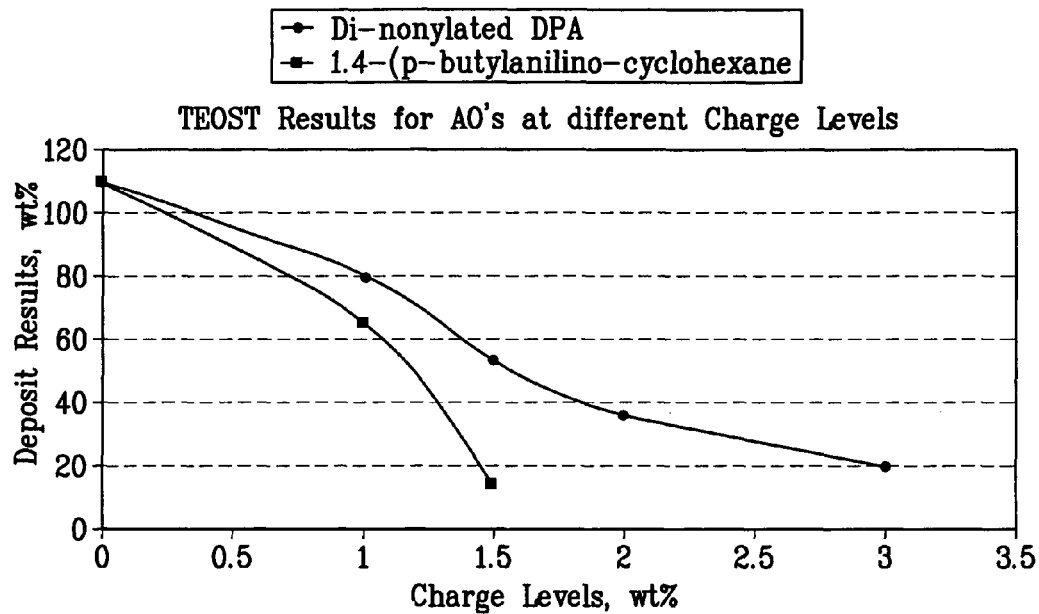
FIG. 1 is a graph comparing wt % deposits against anti-oxidant addition level in the TEOST testing of lubricant compositions containing varying quantities of di-(p-butylanilino)-1,4-cyclohexanes and dinonylated diphenylamines.

The terms "hydrocarbyl radical," "hydrocarbyl" and "hydrocarbyl group" are used interchangeably throughout this document. Likewise the terms "group", "radical", and "substituent" are also used interchangeably in this document. For purposes of this disclosure, "hydrocarbyl radical" is defined to be a radical, which contains hydrogen atoms and up to 32 carbon atoms and which may be linear, branched, or cyclic, and when cyclic, aromatic or non-aromatic. Thus included with the terms "hydrocarbyl radical," "hydrocarbyl" and "hydrocarbyl group" are alkyl, cycloalkyl, alkenyl, alkaryl and arylalkyl groups.

Substituted hydrocarbyl radicals are radicals in which at least one hydrogen atom has been substituted with at least one functional group such as NR*₂, OR* and the like or where at least one non-hydrocarbon atom or group has been inserted within the hydrocarbyl radical, such as —O—, —S—, —N(R*)—, =N— and the like, where R* is independently a hydrocarbyl or halocarbyl radical, and two or more R* may join together to form a substituted or unsubstituted saturated, partially unsaturated or aromatic cyclic or polycyclic ring structure.

In referring to the groups Ar¹ and Ar² as being alkylaromatic groups, it is to be understood that the base aromatic compound can be monocyclic, as in benzene, or can be polycyclic, as, for example, in naphthalene. Moreover, the aromatic compound may be at least partially saturated. In addition, the alkyl group attached to the aromatic compound may be linear, branched or cyclic and may be partially unsaturated. Hetero atoms, such as oxygen, nitrogen and/or sulfur, may also be present.

Described herein are the composition and synthesis of certain novel dialkylanilino-cyclohexane compounds and their use as anti-oxidants in lubricant, fuel and rubber compositions. In particular, these compounds, when added to a lubricant composition, such as a crankcase oil, are found to be more effective in extending the life time oxidative stability of lubricant compositions, such as crankcase oils, than conventional alkylated phenylamines, especially at higher addition levels.

The present dialkylanilino-cyclohexane compounds obey either of the formulae I or II set out below:

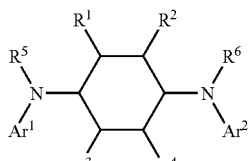

I

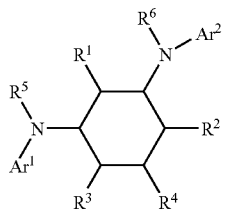

II

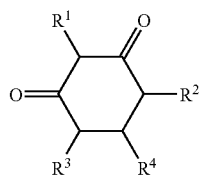

V or the meta homolog using a stoichiometric reducing agent, such as sodium triacetoxyborohydride, or with hydrogen gas and a hydrogenation catalyst as practiced with the reductive alkylation of phenylenediamines with aldehydes and ketones. Another suitable synthesis method involves the reaction of alkyl anilines with cyclohexanediols and a metal dehydrating catalyst such as Raney-nickel at elevated temperatures, such as about 80° C. to about 200° C.

Generally, $R^{10}$ is in the para-position relative to the amine group on the compound of formula (III) and the compound of the formula (IV) or (V) comprises at least one of 1,4-cyclohexanedione and 1,3-cyclohexanedione.

wherein $Ar^1$ and $Ar^2$ can be the same or different and each is an alkylaromatic group; each of $R^1$, $R^2$, $R^3$, and $R^4$ is independently selected from hydrogen or $CR^7R^8$; each of $R^5$, $R^6$, and $R^7$ is independently selected from hydrogen and a substituted or unsubstituted $C_1$ to $C_{32}$ hydrocarbyl group; and each $R^8$ is independently selected from hydrogen and a $C_1$ to $C_2$ alkyl group, provided that when, each of $R^1$ and $R^2$ is $CR^7R^8$ and each such $R^8$ is other than hydrogen, $R^1$ and $R^2$ may be joined to form a five or six-membered ring, and provided further that when, each of $R^3$ and $R^4$ is an adjacent $CR^7R^8$ and each such $R^8$ is other than hydrogen, $R^3$ and $R^4$ may be joined to form a five or six-membered ring.

Conveniently, each of $R^1$, $R^2$, $R^3$, and $R^4$ is hydrogen.

Conveniently, each of $Ar^1$ and $Ar^2$ is an alkylaromatic group in which the alkyl group is a $C_1$ to $C_{30}$ alkyl group, such as a $C_2$ to $C_{20}$ alkyl group, typically with the alkyl group being in the para-position relative to the nitrogen atom attached to the alkylaromatic group. Generally, $Ar^1$ and $Ar^2$ are the same.

Representative compounds having the formulae I or II include para-di(para-n-butylanilino)-cyclohexane, para-di(para-n-hexylanilino)-cyclohexane and para-di(para-n-dodecylanilino)-cyclohexane. Each of these compounds can be present as the cis-form, the trans-form of as a mixture of the cis- and trans-forms.

The present dialkylanilino-cyclohexane compounds are conveniently synthesized by the reductive alkylation of an alkyl aniline of the formula (III):

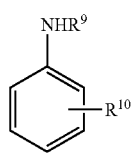

III wherein $R^9$ is $R^5$ or $R^6$ and $R^{10}$ is a $C_1$ to $C_{30}$ alkyl group with a cyclohexanedione compound of the formula (IV) or (V):

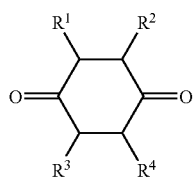

IV

The dialkylanilino-cyclohexane compounds described herein are useful as antioxidants for lubricating oil compositions, typically in an amount between about 0.1 wt % and about 10 wt % of the total lubricating oil composition.

Any suitable oil of lubricating viscosity may be used with the present antioxidants including those oils defined as American Petroleum Institute Groups I, II, and III, and can be of any suitable lubricating viscosity range, for example, having a kinematic viscosity range at 100° C. of about 1.5 centistokes (cSt) to about 1,000 cSt, and preferably about 2 cSt to about 100 cSt. Suitable oils of lubricating viscosity include engine oils, transmission fluids, hydraulic fluids, gear oils, marine cylinder oils, compressor oils, refrigeration lubricants and mixtures thereof. Generally, the lubricating oil composition has a phosphorous content of less than about 0.08 weight percent.

Useful natural oils include mineral lubricating oils such as, for example, liquid petroleum oils, solvent-treated or acid-treated mineral lubricating oils of the paraffinic, naphthenic or mixed paraffinic-naphthenic types, oils derived from coal or shale, animal oils, vegetable oils (e.g., rapeseed oils, castor oils and lard oil), and the like.

Useful synthetic lubricating oils include hydrocarbon oils and halo-substituted hydrocarbon oils such as polymerized and interpolymerized olefins, e.g., polybutylenes, polypropylenes, propylene-isobutylene copolymers, chlorinated polybutylenes, poly(1-hexenes), poly(1-octenes), poly(1-decenes), and the like and mixtures thereof; alkylbenzenes such as dodecylbenzenes; tetradecylbenzenes, dinonylbenzenes, di(2-ethylhexyl)-benzenes, and the like; polyphenyls such as biphenyls, terphenyls, alkylated polyphenyls, and the like; alkylated diphenyl ethers and alkylated diphenyl sulfides and the derivative, analogs and homologs thereof.

Other useful synthetic lubricating oils include liquid polymers of alpha olefins having the proper viscosity. Especially useful synthetic hydrocarbon oils are the hydrogenated liquid oligomers of $C_6$ to $C_{18}$ alpha olefins such as, for example, 1-decene trimer.

Another class of useful synthetic lubricating oils include alkylene oxide polymers, i.e., homopolymers, interpolymers, and derivatives thereof where the terminal hydroxyl groups have been modified by, for example, esterification or etherification. These oils are exemplified by the oils prepared through polymerization of ethylene oxide or propylene oxide, the alkyl and phenyl ethers of these polyoxyalkylene polymers (e.g., methyl poly propylene glycol ether having an average molecular weight of 1,000, diphenyl ether of polyethylene glycol having a molecular weight of 500-1000, diethyl ether of polypropylene glycol having a molecular weight of 1,000-1,500, etc.) or mono- and polycarboxylic esters thereof such as, for example, the acetic esters, mixed $C_3$-$C_8$ fatty acid esters, or the $C_{13}$ oxo acid diester of tetraethylene glycol.

Yet another class of useful synthetic lubricating oils include the esters of dicarboxylic acids e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acids, alkyl malonic acids, alkenyl malonic acids, etc., with a variety of alcohols, e.g., butyl alcohol, hexyl alcohol, dodecyl alcohol, 2-ethylhexyl alcohol, ethylene glycol, diethylene glycol monoether, propylene glycol, etc. Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include, but are not limited to, those made from carboxylic acids having from about 5 to about 12 carbon atoms with alcohols, e.g., methanol, ethanol, etc., polyols and polyol ethers such as neopentyl glycol, trimethylol propane, pentaerythritol, dipentaerythritol, tripentaerythritol, and the like.

Silicon-based oils such as, for example, polyalkyl-, polyaryl-, polyalkoxy- or polyaryloxy-siloxane oils and silicate oils, comprise another useful class of synthetic lubricating oils. Specific examples of these include, but are not limited to, tetraethyl silicate, tetra-isopropyl silicate, tetra-(2-ethylhexyl)silicate, tetra-(4-methyl-hexyl)silicate, tetra-(p-tert-butylphenyl)silicate, hexyl-(4-methyl-2-pentoxy)disiloxane, poly(methyl)siloxanes, poly(methylphenyl)siloxanes, and the like. Still yet other useful synthetic lubricating oils include, but are not limited to, liquid esters of phosphorous containing acids, e.g., tricresyl phosphate, trioctyl phosphate, diethyl ester of decane phosphionic acid, etc., polymeric tetrahydrofurans and the like.

The lubricating oil may be derived from unrefined, refined and rerefined oils, either natural, synthetic or mixtures of two or more of any of these of the type disclosed hereinabove. Unrefined oils are those obtained directly from a natural or synthetic source (e.g., coal, shale, or tar sands bitumen) without further purification or treatment. Examples of unrefined oils include, but are not limited to, a shale oil obtained directly from retorting operations, a petroleum oil obtained directly from distillation or an ester oil obtained directly from an esterification process, each of which is then used without further treatment. Refined oils are similar to the unrefined oils except they have been further treated in one or more purification steps to improve one or more properties. These purification techniques are known to those of skill in the art and include, for example, solvent extractions, secondary distillation, acid or base extraction, filtration, percolation, hydrotreating, dewaxing, etc. Rerefined oils are obtained by treating used oils in processes similar to those used to obtain refined oils. Such rerefined oils are also known as reclaimed or reprocessed oils and often are additionally processed by techniques directed to removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst.

Natural waxes are typically the slack waxes recovered by the solvent dewaxing of mineral oils; synthetic waxes are typically the wax produced by the Fischer-Tropsch process.

If desired, the antioxidant described herein can be used in combination with other additives typically found in lubricating oils and such combinations may, in fact, provide synergistic effects toward improving desired properties, such as improved deposit control, anti-wear, frictional, antioxidant, low temperature, and like properties, to the lubricating oil. Examples of additives found in lubricating oils include, but are not limited to, antioxidants, anti-wear agents, detergents, rust inhibitors, dehazing agents, demulsifying agents, metal deactivating agents, friction modifiers, pour point depressants, antifoaming agents, co-solvents, package compatibilisers, corrosion-inhibitors, dispersants, dyes, extreme pressure agents and mixtures thereof. See, e.g., U.S. Pat. No. 5,498,809 for a description of useful lubricating oil composition additives. When employed with another additive in an additive package for a lubricating oil, the antioxidant described herein is typically present in an amount from 1 to about 75 weight percent of the additive package.

Useful dispersants include, but are not limited to, polyisobutylene succinimides, polyisobutylene succinate esters, Mannich Base ashless dispersants, and the like. Useful detergents include, but are not limited to, metallic alkyl phenates, sulfurized metallic alkyl phenates, metallic alkyl sulfonates, metallic alkyl salicylates, and the like. Useful antioxidant additives for use in combination with the additives of the present invention include, but are not limited to, alkylated diphenylamines, alkylated hindered phenolics, alkylated substituted or unsubstituted phenylenediamines, arylated substituted or unsubstituted phenylenediamines, alkylated oil soluble copper compounds, alkylated sulfur containing compounds known to impart oxidation stability and mixtures thereof. Suitable alkylated sulfur containing compounds known to impart oxidation stability include phenothiazine, sulfurized olefins, thiocarbamates, sulfur bearing hindered phenolics, zinc dialkyldithiophosphates and mixtures thereof.

Useful anti-wear additives for use in combination with the additives of the present invention include, but are not limited to, organo borates, organo phosphites, organic sulfur-containing compounds, zinc dialkyl dithiophosphates, zinc diaryl dithiophosphates, phosphosulfurized hydrocarbons, dialkyldithiophosphate ester, diaryl dithiophosphate ester and mixtures thereof. Useful friction modifiers for use in combination with the additives of the present invention include, but are not limited to, fatty acid esters and amides, organo molybdenum compounds, molybdenum dialkylthiocarbamates, molybdenum dialkyl dithiophosphates, molybdenum disulfide, trimolybdenum cluster dialkyldithiocarbamate, non-sulfur molybdenum compound and mixtures thereof. Useful antifoaming agents include, but are not limited to, polysiloxane, and the like. An example of a rust inhibitor is polyoxyalkylene polyols, and the like. Useful VI improvers include, but are not limited to, olefin copolymers and dispersant olefin copolymers, and the like. An example of a pour point depressant is polymethacrylate, and the like.

The dialkylanilino-cyclohexane compounds described herein are also useful as antioxidants for fuel compositions, typically in an amount between about 10 ppm and about 1000 ppm of the total fuel composition.

Suitable fuels include any internal combustion engine hydrocarbon fuel, e.g., diesel, gasoline, kerosene, jet fuels, etc.; alcoholic fuels such as methanol or ethanol; or a mixture of any of the foregoing. When the fuel is diesel, such fuel generally boils above about 212° F. (100° C.). The diesel fuel can comprise atmospheric distillate or vacuum distillate, or a blend in any proportion of straight run and thermally and/or catalytically cracked distillates.

When the fuel is gasoline, it can be derived from straight-chain naphtha, polymer gasoline, natural gasoline, catalytically cracked or thermally cracked hydrocarbons, catalytically reformed stocks, etc. It will be understood by one skilled in the art that gasoline fuels typically boil in the range of about 80° F. to about 450° F. (27° C. to 232° C.) and can contain straight chain or branched chain paraffins, cycloparaffins, olefins, aromatic hydrocarbons, and any mixture of these.

The dialkylanilino-cyclohexane compounds described herein are also useful as antioxidants for natural and synthetic polymers and rubbers, for example, polymers of butadiene and copolymers thereof with styrene or acrylonitrile, and isoprene or chloroprene polymers. When used as a rubber antioxidant, the present compounds are typically present in an amount between about 0.5 wt % and about 8.0 wt % of the total rubber composition.

In addition, the dialkylanilino-cyclohexane compounds described herein can be used as stabilizers for other organic materials subject to oxidative, thermal, and/or light-induced degradation and in need of stabilization to prevent or inhibit such degradation. Examples of such organic materials include polyols, urethanes, reaction products of polyols and urethanes, plastics, greases, roof sheeting, cables, gaskets, seals, compounded tires and rubber belts.

The invention will now be more particularly described with reference to the Examples and the accompanying drawings.

EXAMPLE 1

Preparation of di-(p-butylanilino)-1,4-cyclohexanes

In a 100 ml reaction vessel, equipped with a mechanical stirrer, nitrogen blanket, reflux condenser and thermocouple are charged 1,4-cyclohexanedione (2.5 grams, 0.022M), p-nbutyl aniline (7.5 grams, 0.050M), glacial acetic acid (1.5 grams, 0.025M) and 30 ml of tetrahydrofuran (THF). To this stirring solution at room temperature is added 6.5 grams (0.0305M) of sodium triacetoxyborohydride (STAB-H) all at once. The reaction may exotherm up to 50° C. over 5 minutes. The temperature is this slowly raised to 60° C. and held for one hour with vigorous stirring. The temperature is then lowered to 25° C. where a second 6.5 gram portion of STAB-H is added. The temperature is then raised again to 60° C. with vigorous stirring and held at 60° C. for two hours. At this point STAB salt balls may fall out of solution, at which point more THF may have to added and the salt balls broken up.

After the reaction is complete, the temperature is reduced to 30° C. and the reaction solution is diluted with 100 ml of ethyl acetate and transferred to a separatory funnel. The product solution is then washed with three 50 ml portions of 5% aqueous NaOH, one 50 ml portion of 5% aqueous sodium carbonate and two 50 ml portions of water before drying the organic layer over anhydrous magnesium sulfate. The dried solution is filtered and the solvents removed under vacuum to yield 8.5 grams of a reddish viscous liquid. This liquid is then passed through a 1 by 4 inch column of silica gel using hexanes initially as the column solvent. The starting reactants and by-products pass through the column first. The column solvent is then changed to 10-20% THF in hexanes to flush the desired products off the column. The product is a mixture of the cis and trans p-cyclohexane isomers which may solidify slowly on standing. The amount of product collected is 4.6 grams. Some of the trans isomer can be separated from the isomer mixture by recrystallization from hot methanol.

EXAMPLE 2

Preparation of di-(p-dodecylanilino)-1,4-cyclohexanes

In a 100 ml reaction vessel, equipped with a mechanical stirrer, nitrogen blanket, reflux condenser and thermocouple are charged 1,4-cyclohexanedione (2.4 grams, 0.021M), p-dodecylaniline (13 grams, 0.050M), glacial acetic acid (1.0 grams, 0.016M) and 30 ml of THF. To this stirring solution at room temperature is added 7.2 grams (0.031M) of sodium triacetoxyborohydride (STAB-H) all at once. The reaction may exotherm up to 50° C. over 5 minutes. The temperature is this slowly raised to 60° C. and held for one hour with vigorous stirring. The temperature is then lowered to 25° C. where a second 5.2 gram (0.24M) portion of STAB-H is added. The temperature is then raised again to 60° C. with vigorous stirring and held at 60° C. for two hours. At this point STAB salt balls may fall out of solution, at which point more THF may have to added and the salt balls broken up.

After the reaction is complete, the temperature is reduced to 30° C. and the reaction solution is diluted with 100 ml of hexanes and transferred to a separatory funnel. The product solution is then washed with three 50 ml portions of 5% aqueous NaOH, one 50 ml portion of 5% aqueous sodium carbonate and two 50 ml portions of water before drying the organic layer over anhydrous magnesium sulfate. The dried solution was filtered and the solvents removed under vacuum to yield 8.5 grams of a reddish viscous liquid. This liquid is then passed through a 2 by 8 inch column of silica gel using hexanes initially as the column solvent. The starting reactants and by-products pass through the column first. The column solvent is then changed to a 5% THF in hexanes to flush the desired products off the column. The product is a mixture of the cis and trans p-cyclohexane isomers. The product is a viscous dark burgundy colored liquid.

EXAMPLE 3

Preparation of di-(p-hexylanilino)-1,4-cyclohexanes

In a 250 ml reaction vessel, equipped with a mechanical stirrer, nitrogen blanket, reflux condenser and thermocouple are charged 1,4-cyclohexanedione (5.0 grams, 0.044M), p-nhexylaniline (17.7 grams, 0.10M), glacial acetic acid (1.5 grams, 0.025M) and 75 ml of THF. To this stirring solution at room temperature are added 13 grams (0.06M) of sodium triacetoxyborohydride (STAB-H) all at once. The reaction may exotherm up to 50° C. over 5 minutes. The temperature is this slowly raised to 60° C. and held for one hour with vigorous stirring. The temperature is then lowered to 25° C. where a second 13 gram (0.06M) portion of STAB-H is added. The temperature is then raised again to 60° C. with vigorous stirring and held at 60° C. for one and half hours. At this point STAB salt balls may fall out of solution, at which point more THF may have to added and the salt balls broken up.

After the reaction is complete, the temperature is reduced to 30° C. and the reaction solution is diluted with 120 ml of ethyl acetate and transferred to a separatory funnel. The product solution is then washed with three 50 ml portions of 5% aqueous NaOH, one 50 ml portion of 5% aqueous sodium carbonate and two 50 ml portions of water before drying the organic layer over anhydrous magnesium sulfate. The dried solution is filtered and the solvents removed under vacuum to yield 8.5 grams of a reddish viscous liquid. An approx. 10 gram portion of this liquid is then passed through a 2 by 6 inch column of silica gel using 1% THF in hexanes initially as the column solvent. The starting reactants and by-products pass through the column first. The column solvent is then changed to a 3% THF in hexanes to flush the desired products off the column. The product is a 5 gram mixture of the cis and trans p-cyclohexane isomers. The product is a viscous dark burgundy colored liquid which may slowly solidify on standing. Some of the trans isomer can be separated from the isomer mixture by recrystallization from hot methanol.

EXAMPLE 4

Comparison of di-(p-butylanilino)-1,4-cyclohexanes and dinonylated diphenylamines as Antioxidants in Lubricant Compositions A series of lubricant compositions were produced by mixing a fully formulated motor oil (without antioxidant) with varying amounts of the di-(p-butylanilino)-1,4-cyclohexane mixture of Example 1 and the oxidative stability of the resulting compositions were measured by the Thermo-Oxidation Engine Oil Simulation Test (TEOST) and by High-Pressure Differential Scanning Calorimetry (PDSC).

The TEOST is a test to measure the ability of an antioxidant to prevent thermal breakdown of an oil to cause deposits to form on a heated (285° C.) metal rod, wherein the deposits are measured in milligrams at the end of a 24 hour test run. The higher the amount of deposits measured, the lower the oxidative stability of the oil. Full details of the TEOST test can be found in ASTM MHT-4. The specific parameters are shown below.

| TEOST Parameters | |
|---|---|
| Rod Temperature | 285 C. |
| Oil Pump Setting | 247 |
| Oil Volume | 8.4 grams |
| Dry Air Flow Rate | 10 ml/minute |
| Catalyst (Tannis Part 5953) | 0.1 gram. |

The PDSC data presented is a measure of the oxidation induction time (OIT) of each oil or sample blend. The PDSC method employs a steel bomb under pressure and the catalyst is oil soluble iron derived from iron naphthanate. At the start of a run the PDSC cell is initially heated at a rate of 40° C./min to the isothermal temperature listed below. The induction time is measured from the time the sample reaches its isothermal temperature until the enthalpy change is observed. The longer the oxidation induction time the better the oxidation stability of the oil. The PDSC instrument used is a Mettler DSC27HP manufactured by Mettler-Toledo, Inc. The test has a repeatability of about ±2.5 minutes with 95% confidence for OIT's less than 100 min. Each data point reported is the average of at least two runs on a single test blend or multiple blends. The PDSC conditions are given below.

| PDSC Parameters | |
|---|---|
| Temperature | 200° C. |
| Gas | Oxygen |
| Flow Rate | 100 ml/min |
| Pressure | 500 psi |
| Sample Size | 1.5 mg |
| Pan (open/closed) | open |

Figure 2:
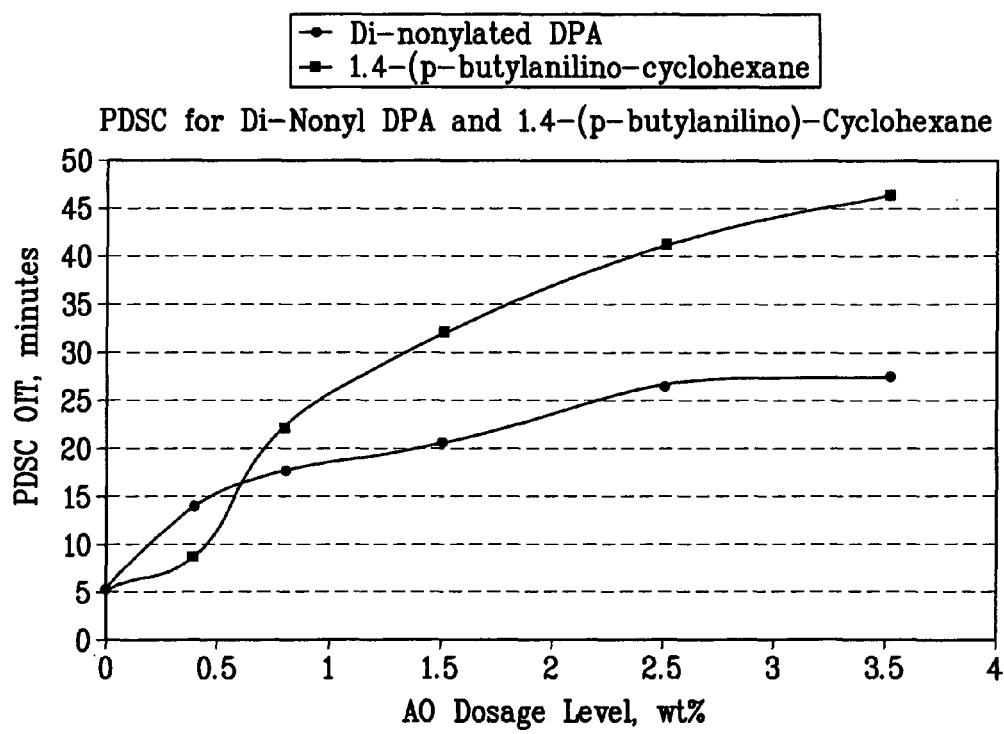
FIG. 2 is a graph comparing oxidation induction time (OIT), min against anti-oxidant addition level in the PDSC testing of lubricant compositions containing varying quantities of di-(p-butylanilino)-1,4-cyclohexanes and dinonylated diphenylamines.

For comparison, the same tests were conducted on a separate series of the compositions produced by mixing the previous identical fully formulated motor oil (without antioxidant) with the same varying amounts of a conventional dinonylated diphenylamine anti-oxidant. The results of the tests are shown in Tables 1 and 2 and in FIGS. 1 and 2.

TABLE 1

| TEOST Results | | | | | |
|---|---|---|---|---|---|
| | Anti-Oxidant charge level, wt % | | | | |
| Deposits, mg | 0 | 1 | 1.5 | 2 | 3 |
| Di-nonylated DPA | 110 | 79 | 53 | 36 | 20 |
| 1,4-(p-butylanilino)-cyclohexane | 110 | 65 | 14 | | |

TABLE 2

| PDSC Results | | | | | |
|---|---|---|---|---|---|
| Oxidation Induction Time (OIT), | Anti-Oxidant charge level, wt % | | | | |
| min. | 0 | 0.4 | 0.8 | 1.5 | 2.5 |
| Di-nonylated DPA | 5.45 | 13.86 | 17.61 | 20.48 | 26.4 |
| 1,4-(p-butylanilino)-cyclohexane | 5.45 | 8.71 | 22.05 | 31.92 | 40.86 |

The results demonstrate that the di-(p-butylanilino)-1,4-cyclohexane mixture of Example 1 is more effective in extending and improving oxidation stability of the lubricant tested as compared with the conventional dinonylated diphenylamine anti-oxidant, particularly at higher addition levels.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A dialkylanilino-cyclohexane compound having the following formula I or formula II:

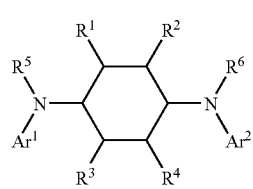

I

-continued

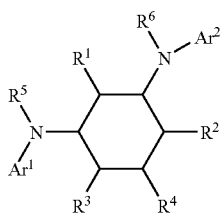

II wherein $Ar^1$ and $Ar^2$ can be the same or different and each is selected from alkylphenyl and alkylnaphthyl wherein said alkyl is a $C_4$ to $C_{12}$ alkyl group; each of $R^1$, $R^2$, $R^3$, and $R^4$ is independently selected from hydrogen or $CR^7R^8$, each of $R^5$ and $R^6$ is independently selected from hydrogen and an unsubstituted $C_1$ to $C_{32}$ hydrocarbyl group; $R^7$ is selected from hydrogen and a substituted or unsubstituted $C_1$ to $C_{32}$ hydrocarbyl group; and each $R^8$ is independently selected from hydrogen and a $C_1$ to $C_2$ alkyl group, provided that when, each of $R^1$ and $R^2$ is $CR^7R^8$ and each such $R^8$ is other than hydrogen, $R^1$ and $R^2$ may be joined to form a five or six-membered ring, and provided further that when, each of $R^3$ and $R^4$ is an adjacent $CR^7R^8$ and each such $R^8$ is other than hydrogen, $R^3$ and $R^4$ may be joined to form a five or six-membered ring.

2. The compound of claim 1, wherein each of $R^1$, $R^2$, $R^3$, and $R^4$ is hydrogen.

3. The compound of claim 1, wherein each of $Ar^1$ and $Ar^2$ is an alkylphenyl in which the alkyl group is in the para-position relative to the nitrogen atom attached to the alkylaromatic group.

4. The compound of claim 1, wherein each of $Ar^1$ and $Ar^2$ is the same alkylaromatic group.

5. The compound of claim 1, wherein the compound is selected from para-di(para-n-butylanilino)-cyclohexane, para-di(para-n-hexylanilino)-cyclohexane and para-di(para-n-dodecylanilino)-cyclohexane.

6. A lubricating oil composition comprising (a) at least one oil of lubricating viscosity and (b) a dialkylanilino-cyclohexane compound having the following formula I or II:

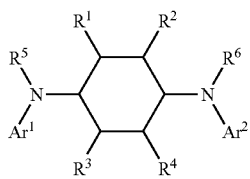

I

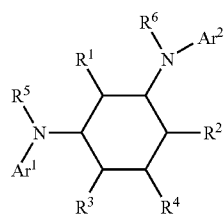

II wherein $Ar^1$ and $Ar^2$ can be the same or different and each is selected from alkylphenyl and alkyinaphthyl wherein the alkyl group is a $C_4$ to $C_{12}$ alkyl group; each of $R^1$, $R^2$, $R^3$, and $R^4$ is independently selected from hydrogen or $CR^7R^8$; each of $R^5$ and $R^6$ is independently selected from hydrogen and an unsubstituted $C_1$ to $C_{32}$ hydrocarbyl group; $R^7$ is selected from hydrogen and a substituted or unsubstituted $C_1$ to $C_{32}$ hydrocarbyl group; and each $R^8$ is independently selected from hydrogen and a $C_1$ to $C_2$ alkyl group, provided that when, each of $R^1$ and $R^2$ is $CR^7R^8$ and each such $R^8$ is other than hydrogen, $R^1$ and $R^2$ may be joined to form a five or six-membered ring, and provided further that when, each of $R^3$ and $R^4$ is an adjacent $CR^7R^8$ and each such $R^8$ is other than hydrogen, $R^3$ and $R^4$ may be joined to form a five or six-membered ring.

7. The lubricating oil composition of claim 6 wherein said dialkylanilino-cyclohexane compound is present in an amount between about 0.1 wt % and about 10 wt % of the total lubricating oil composition.

8. The lubricating oil composition of claim 6, wherein the at least one oil of lubricating viscosity is selected from the group consisting of engine oils, transmission fluids, hydraulic fluids, gear oils, marine cylinder oils, compressor oils, refrigeration lubricants and mixtures thereof.

9. The lubricating oil composition of claim 6, wherein the at least one oil of lubricating viscosity has a viscosity of about 1.5 to about 2000 centistokes (cSt) at 100° C.

10. The lubricating oil composition of claim 6, further comprising at least one lubricating oil additive.

11. The lubricating oil composition of claim 6, further comprising at least one lubricating oil additive selected from the group consisting of antioxidants, anti-wear agents, detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and mixtures thereof.

12. The lubricating oil composition of claim 6, further comprising at least one lubricating oil additive selected from the group consisting of an alkylated diphenylamine, alkylated hindered phenolic, alkylated substituted or unsubstituted phenylenediamine, arylated substituted or unsubstituted phenylenediamine, alkylated oil soluble copper compound, alkylated sulfur containing compound known to impart oxidation stability and mixtures thereof.

13. The lubricating oil composition of claim 12, wherein the alkylated sulfur containing compound known to impart oxidation stability is selected from the group consisting of a phenothiazine, sulfurized olefin, thiocarbamate, sulfur bearing hindered phenolic, zinc dialkyldithiophosphate and mixtures thereof.

14. The lubricating oil composition of claim 6, further comprising at least one lubricating oil additive selected from the group consisting of a fatty acid ester or amide, organo molybdenum compound, molybdenum dialkyldithiocarbamate, molybdenum dialkyl dithiophosphate, molybdenum disulfide, tri-molybdenum cluster dialkyldithiocarbamate, non-sulfur molybdenum compound and mixtures thereof.

15. The lubricating oil composition of claim 6, further comprising at least one lubricating oil additive selected from the group consisting of a zinc dialkyldithiophosphate, zinc diaryldithiophosphate, dialkyldithiophosphate ester, diaryl dithiophosphate ester and mixtures thereof.

16. The lubricating oil composition of claim 6, having a phosphorous content of less than about 0.08 weight percent.

17. A fuel composition comprising (a) a base fuel and (b) a dialkylanilino-cyclohexane compound having the following formula I or II:

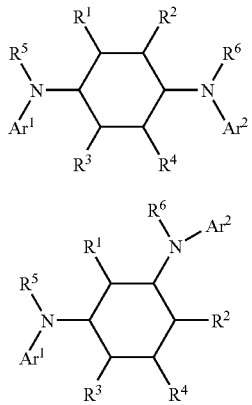

wherein $Ar^1$ and $Ar^2$ can be the same or different and each is selected from alkylphenyl and alkylnaphthyl wherein the alkyl group is a $C_4$ to $C_{12}$ alkyl group; each of $R^1$, $R^2$, $R^3$, and $R^4$ is independently selected from hydrogen or $CR^7R^8$; each of $R^5$ and $R^6$ is independently selected from hydrogen and an unsubstituted $C_1$ to $C_{32}$ hydrocarbyl group: $R^7$ is selected from hydrogen and a substituted or unsubstituted $C_1$, to $C_{32}$ hydrocarbyl group; and each $R^8$ is independently selected from hydrogen and a $C_1$, to $C_2$ alkyl group, provided that when, each of $R^1$ and $R^2$ is $CR^7R^8$ and each such $R^8$ is other than hydrogen, $R^1$ and $R^2$ may be joined to form a five or six-membered ring, and provided further that when, each of $R^3$ and $R^4$ is an adjacent $CR^{7R8}$ and each such $R^8$ is other than hydrogen, $R^3$ and $R^4$ may be joined to form a five or six-membered ring.

18. The composition of claim 17 wherein said dialkylanilino-cyclohexane compound is present in an amount between about 10 ppm and about 1000 ppm of the total fuel composition.

19. A rubber composition comprising (a) a base rubber and (b) a dialkylanilino-cyclohexane compound having the following formula I or II:

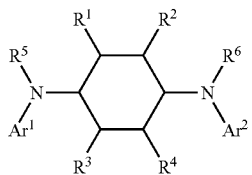

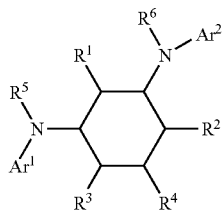

wherein $Ar^1$ and $Ar^2$ can be the same or different and each is selected from alkylphenyl and alkylnaphthyl wherein the alkyl group is a $C_4$ to $C_{12}$ alkyl group; each of $R^1$, $R^2$, $R^3$, and $R^4$ is independently selected from hydrogen or $CR^7R^8$; each of $R^5$ and $R^6$ is independently selected from hydrogen and an unsubstituted $C_1$ to $C_{32}$ hydrocarbyl group; $R^7$ is selected from hydrogen and a substituted or unsubstituted $C_1$ to $C_{32}$ hydrocarbyl group; and each $R^8$ is independently selected from hydrogen and a $C_1$, to $C_2$ alkyl group, provided that when, each of $R^1$ and $R^2$ is $CR^7R^8$ and each such $R^8$ is other than hydrogen, $R^1$ and $R^2$ may be joined to form a five or six-membered ring, and provided further that when, each of $R^3$ and $R^4$ is an adjacent $CR^7R^8$ and each such $R^8$ is other than hydrogen, $R^3$ and $R^4$ may be joined to form a five or six-membered ring.

20. The composition of claim 19 wherein said dialkylanilino-cyclohexane compound is present in an amount between about 0.5 wt % and about 8.0 wt % of the total rubber.

21. A stabilizer-containing composition comprising (a) an organic material subject to oxidative, thermal, and/or light-induced degradation and in need of stabilization to prevent or inhibit such degradation; and (b) a stabilization effective amount of the dialkylanilino-cyclohexane compound of claim 1.

22. The stabilizer-containing composition of claim 21, wherein the organic material is a natural or synthetic polymer.

23. The stabilizer-containing composition of claim 21, wherein the organic material is selected from the group consisting of a polyol, urethane, reaction product of a polyol and urethane, plastic, grease, roof sheeting, motor oil, cable, gasket, seal, compounded tire and rubber belt.

* * * * *